United States Patent
Pennings et al.

(10) Patent No.: US 6,846,875 B2
(45) Date of Patent: Jan. 25, 2005

(54) HYDROGELS AND METHODS FOR THEIR PRODUCTION

(75) Inventors: Albert Johan Pennings, Maaseik (BE); Coenraad Jan Spaans, Alkmaar (NL); Jacqueline Hermina deGroot, Leek (NL)

(73) Assignee: Pharmacia Groningen BV, Groningen (NL)

( * ) Notice: Subject to any disclaimer, the term of this patent is extended or adjusted under 35 U.S.C. 154(b) by 254 days.

(21) Appl. No.: 09/829,861

(22) Filed: Apr. 10, 2001

(65) Prior Publication Data

US 2002/0034547 A1 Mar. 21, 2002

Related U.S. Application Data

(60) Provisional application No. 60/197,495, filed on Apr. 14, 2000.

(30) Foreign Application Priority Data

Apr. 10, 2001 (SE) .............................................. 0001309

(51) Int. Cl.[7] ............................................ C08F 122/26
(52) U.S. Cl. ........................ 524/557; 524/589; 524/590; 351/160 H; 623/11.11; 623/6.59
(58) Field of Search ................................ 524/557, 589, 524/590; 351/160 H; 623/11.11, 6.59

(56) References Cited

U.S. PATENT DOCUMENTS

| | | | |
|---|---|---|---|
| 4,598,122 A | * | 7/1986 | Goldenberg ................. 525/61 |
| 4,664,857 A | | 5/1987 | Nambu |
| 4,840,992 A | * | 6/1989 | Ofstead ....................... 525/61 |
| 4,978,713 A | | 12/1990 | Goldenberg |
| 5,135,965 A | * | 8/1992 | Tahan ......................... 523/106 |
| 5,210,111 A | * | 5/1993 | Goldenberg et al. ........ 523/108 |
| 5,439,950 A | | 8/1995 | Liao et al. |
| 5,480,950 A | | 1/1996 | Wang et al. |
| 5,633,299 A | | 5/1997 | Van Druten et al. |
| 5,719,260 A | | 2/1998 | Van Der Heide |
| 6,262,208 B1 | * | 7/2001 | Makabe et al. ............. 526/245 |

FOREIGN PATENT DOCUMENTS

| | | |
|---|---|---|
| EP | 0216074 | 4/1987 |
| EP | 0322976 | 7/1989 |
| EP | 0530140 | 3/1993 |
| EP | 0918233 | 5/1999 |
| EP | 1000726 | 5/2000 |

* cited by examiner

*Primary Examiner*—David W. Wu
*Assistant Examiner*—Satya B Sastri
(74) *Attorney, Agent, or Firm*—Dinsmore & Shohl LLP

(57) ABSTRACT

The present invention relates to new hydrogels with improved mechanical properties and methods of their preparation. The hydrogels are formed from hydrophilic polymers having function hydroxyl groups and have low elasticity modulus typically less than about 10 kPa, a tensile strength above 1 MPa, an elongation above 50% which makes suitable as medical implants, in particular intraocular lenses. The hydrogels are prepared by a crosslinking method with a comparatively low concentration of hydrophilic polymer of a sufficiently high molecular weight dissolved in a good solvent.

33 Claims, 7 Drawing Sheets

HYDROGELS AND METHODS FOR THEIR PRODUCTION

This application claims the benefit of 60/197,495 filed on Apr. 14, 2000.

BACKGROUND OF THE INVENTION

Hydrogels have found numerous applications in medical technology, for examples in implants or as drug delivery devices. A drawback with conventional hydrogels, such as polyHEMA (hydroxyethylmethacrylate), is their brittleness due to their low tensile strength in swollen state, which is about 0.5 MPa. This characteristic is especially problematic during surgical intervention when an implant made from a hydrogel material shall be inserted into the body often with complex manipulations, as is the case when a hydrogel intraocular lens (IOL) shall be positioned in the capsular bag of the eye through a small incision. Another drawback for the application of conventional hydrogels as medical implants is their high elasticity modulus. In the technique of replacing the natural lens of the eye with a hydrogel IOL, their high modulus prevents the implant from being accommodatable under the influence of the compressing and relaxing forces exerted by the ciliary muscles. It is also prerequisite in an ophthalmic application that the refractive index should be sufficiently high. This implies that the swollen network should contain a sufficient amount of water.

Obviously there is a demand for new hydrogel materials that can overcome the mentioned disadvantages.

It is the object of the present invention to provide for hydrogels, which at a high water content have suitably high tensile strength and sufficiently low elasticity modulus to improve their usefulness as medical implants.

It is also an object of the present invention to provide for a method of preparing such hydrogels.

DESCRIPTION OF THE INVENTION

The present invention refers to new hydrogels with improved mechanical characteristics that makes them highly applicable as implants in the human body. In this context hydrogel is defined as a polymer composition that is swellable in water to an equilibrium value. Such a polymer composition comprises a network of a hydrophilic polymer. A network of a hydrophilic polymer typically means that crosslinks are formed between polymer chains by covalent bonds or by physical bonds, e.g. hydrogen bonds. A hydrophilic polymer according to the present invention is defined as a polymer capable of swelling in water, however, not being soluble in water. The hydrophilic polymer is generally described to have a carbon to carbon backbone —(C—C—C—C)$_n$— to which functional groups having an active hydrogen are attached so the polymer is provided with hydrophilic characteristics and points for crosslinking. According to a highly preferred aspect of the present invention, the functional groups are hydroxyl groups. The hydroxyl groups can either be attached directly to the carbon to carbon backbone or be a functional group in a chain attached to said backbone thus providing a polyhydroxy polymer. Preferably, this type of hydrophilic polymers has no other functional groups than hydroxyl. Especially suitable such hydrophilic polymers are found among the following: —(CH$_2$—CHOH)$_n$—(polyvinyl alcohol); —(CH$_2$—CH$_2$)$_n$(CH$_2$—CHOH)$_m$—(copolymer of ethylene and vinyl alcohol); —(CH$_2$—CH$_2$—CHOH)$_n$— and —(CH$_2$—CH(CH$_2$OH))$_n$— (polyallyl alcohol). Polyvinyl alcohol is normally a water-soluble polymer and within this context it is therefore subjected to chemical modification to obtain hydrophilic properties according the earlier given definition. These mentioned polymers and their methods of production are well known to the skilled practitioner and will not be discussed here in greater detail. It would be conceivable for the person skilled in polymer chemistry to select suitable qualities of these polymers to be applicable within the context of the present invention. It is also to be understood that functional analogues and derivatives of the mentioned suitable polymers shall be regarded to be a part of the present invention when it is described in more general terms.

The present invention in its most general form refers to hydrogels comprising a network of hydrophilic polymers having hydroxyl group carrying carbon-carbon backbones having specifically advantageous mechanical characteristics making suitable as implants, especially ocular implants. The hydrogels typically have an elasticity modulus less than about 10 kPa, preferably less than about 5 kPa which is sufficiently low to render them useful as accommodatable intraocular lenses. Furthermore, the hydrogels have an elongation of at least 50% at equilibrium water content and a tensile strength of at least about 1 MPa, suitably above about 5 MPa, which provides them a sufficient strength so thin foldable implants (e.g. intraocular lenses) can be produced. The hydrogels can be made with a sufficient optical clarity, so as to obtain an optical transmission of at least about 40% and a suitably high a refractive index of at least about 1.40.

It is an important feature of the present invention that the hydrophilic polymers from which the hydrogels are formed have sufficiently high individual molecular weight. It has been found that an insufficient molecular weight of the hydrophilic polymers forming the hydrogels can impair both the strength and optical quality and create flaws in the products. Therefore it is suitable that the molecular weight is at least 200 000.

Preferably, the molecular weight is at least 300 000, before they are assembled in a network by, for example a crosslinking reaction. The relationship between molecular weight and crosslinking density will be discussed below in more detail.

The inventive hydrogels have a general polymer content between about 30 to 80% (wt), preferably between about 40 to 70% (wt) and more preferably between about 40 to 60%.

According to an embodiment of the present invention, the hydrophilicity of the polymers is reduced by chemically modifying the hydrophilic polymers. Thereby, the equilibrium water content of the hydrogels is reduced. This step can be necessary for certain water-soluble polymers before they are applicable in the inventive context and will comply with the definition of "hydrophilic" as given above. An example of such a polymer is poly(vinylalcohol). A suitable agent for such chemical modification is a monoisocyanate capable of reacting with the hydroxyl groups of the hydrophilic polymers. Suitable such monoisocyanates are found among lower alkyl, aryl or arylalkyl isocyanates. One example of a suitable monoisocyanate is n-butylisocyanate, or if a less hydrophobic isocyanate is preferred ethylisocyanate. Preferably, this type of modification is random along the polymer backbone.

Suitable hydrophilic polymers for the hydrogels are selected among polymers having a carbon to carbon backbone only substituted with hydrogen, hydroxyl and hydroxyalkyl, wherein alkyl is a lower alkyl having six or less carbon atoms. A preferred hydroxyalkyl is hydroxymethyl. Especially suitable are at least one of the polymers —(CH$_2$—CHOH)$_n$—(polyvinyl alcohol); —(CH$_2$—CH$_2$)$_n$(CH$_2$—CHOH)$_m$—(copolymer of ethylene and vinyl alcohol); —(CH$_2$—CH$_2$—CHOH)$_n$—(poly(1-hydroxy-1,3-propanediyl) and —(CH$_2$—CH(CH$_2$OH))$_n$—(polyallylalcohol). Consequently it is preferred that the hydrogels includes one of these polymers.

According to a preferred embodiment the network of the hydrogels is formed by crosslinks in the form of covalent bonds between the hydrophilic polymers. In one first preferred aspect of this embodiment, the crosslinks are formed by reacting hydroxyl groups of the hydrophilic polymers with a crosslinkable amount of a diisocyanate having a general formula ONC—R—CNO, thereby providing urethane bonds —O—C(O)—NH—R—NH—C(O)—O— between the polymer chains, wherein R is a spacing group. R can be an optionally substituted lower alkyl group having between one and ten carbon atoms, such as —(CH$_2$)$_4$—. Suitable diisocyanates for the crosslinking are 1,4-butanediisocyante, 1,6-hexanediisocyanate and lysine-diisocyanate and the diisocyanate having the formula OCN—(CH$_2$)$_4$—NH—C(O)O—(CH$_2$)$_4$—O(O)C—NH—(CH$_2$)$_4$—CNO with a preference for 1,4-butanediisocyanate. The skilled person in this field will be able to find alternative diisocyanates to these mentioned and yet operate within the context of the invention. In a second aspect of this embodiment the crosslinks can be formed by epoxy-compound, such as epichlorohydrine or isophorone. An epoxy-compound useful in this context preferably has two epoxy groups spaced apart by a suitable chain. It is a characteristic feature of this embodiment that the crosslinking density is kept low, preferably it less than about 10%, preferably less than 5%. In some applications the crosslinking density can be reduced to 3% and even to 1%, given that the specifically mentioned important mechanical characteristics of the resulting hydrogels in such a case can be retained or improved by correspondingly increasing the molecular weight of the hydrophilic polymers. It is found within the context of the present invention that suitable hydrogels can be obtained with very low crosslinking density such as in the range of about 0.5 to 3% if the molecular weight of hydrophilic polymers is correspondingly increased. A particularly suitable hydrogel comprises crosslinked poly(1-hydroxy-1,3-propanediyl) which optionally has been modified before crosslinking with a low degree (less than 10%) of monoisocyanate to modulate its hydrophilicity (i.e. equilibrium water content). Suitably, the poly(1-hydroxy-1,3-propanediyl) is crosslinked with a lower alkyl diisocyante, most suitably 1,4-butanediisocyanate. A specific example of a hydrogel according to the present invention is based on poly(1-hydroxy-1,3-propanediyl) having about 5% of its hydroxyl groups modified with n-butyl-isocyanate and crosslinked with 1,4-butanediisocyante to densities varying between 1 and 5%. Such a hydrogel is found to have excellent mechanical and optical properties, which are particularly desirable in intraocular lenses capable of undergo accommodation when subjected to the forces of ciliary muscles of the eye.

In another embodiment of the invention the hydrogels comprise polyallylalcohol as a hydrophilic polymer in the network without crosslinks (i.e. covalent bonds) between the polymer chains. In this alternative, the characteristics of the hydrogel can optionally be controlled by the amount of chemical modification (e.g. amount introduced monoisocyanate groups) of the hydrophilic polymer chains and the molecular weight of the polymer.

The present invention is also directed to a method of preparing hydrogels with low elasticity moduli. The inventive method is based on the findings that a hydrogel with surprisingly low modulus is obtainable if a low concentration of the polymer and sufficiently high molecular weight is selected for the preparation process. Hydrogels with elasticity moduli as low as below about 10 kPa, or even below about 5 kPa are attainable with the inventive method, while yet obtaining excellent other mechanical and optical characteristics of the hydrogel including a sufficiently high tear strength.

In a general form, the method comprises the steps of selecting hydrophilic polymer of sufficiently high molecular weight; dissolving said polymer in a good solvent to a concentration not exceeding about 5% (wt); adding a crosslinking agent; mixing and reacting polymer with crosslinker; evaporating said solvent and finally optionally adding water. A good solvent is defined herein to be a solvent which is capable of generating a minimum amount of trapped entanglements and entangled polymer chain ends, so the polymer chains are stretched out rather than collapsed. Trapped entanglements, loops and problems with dangling polymer chain ends can be avoided with a good solvent. Thereby flaws and other network defects in hydrogel will be reduced to a minimum, so a more homogenous network is formed. It is also an important aspect of the inventive method to select a sufficiently high molecular weight of the hydrophilic polymers. It is suitable that the hydrophilic polymer has a molecular weight of at least about 200 000, preferably at least about 300 000. A sufficiently high molecular weight will contribute to improve the homogeneity of the network by reducing the amount of dangling polymer chain ends. The hydrophilic polymers suitable to employ in the inventive method are found among polymers having a carbon to carbon backbone to which functional hydroxyl groups for crosslinking are attached. In a general meaning the method is applicable also for other types of hydrophilic polymers having other types of functional groups for crosslinking given that the above mentioned general requirements are met. Suitable hydrophilic polymers for the hydrogels are selected among polymers having a carbon to carbon backbone only substituted with hydrogen, hydroxyl and hydroxyalkyl, wherein alkyl is a lower alkyl having six or less carbon atoms. A preferred hydroxyalkyl is hydroxymethyl. Especially suitable is at least one of the polymers —(CH$_2$—CHOH)$_n$—(polyvinyl alcohol); —(CH$_2$—CH$_2$(CH$_2$—CHOH)$_m$—(copolymer of ethylene and vinyl alcohol); —(CH$_2$—CH$_2$—CHOH)$_n$—(poly(1-hydroxy-1,3-propanediyl)) and —(CH$_2$—CH(CH$_2$OH))$_n$—(polyallylalcohol). According one embodiment of the inventive method, the hydrophilic properties of the polymers is reduced in advance of the crosslinking by chemical modification. The modification of the hydrophilic properties is preferably performed by reacting a fraction of the hydroxyl groups of the polymers with monoisocyanate. The degree of modification is suitably less than 15% and preferably less than 10%. In one example poly(1-hydroxy-1,3-propanediyl is modified to a degree of about 5%. Suitable monoisocyanates for this step of the method have been discussed earlier in the specification. Suitable crosslinkers have also been discussed earlier. One example is diisocyanates having a formula OCN—R—CNO defined as above. An example of such a suitable diisocyanate is 1,4-butane-diisocyanate.

Furthermore, the inventive method involves steps of degassing the solution of polymer in good solvent before conducting the crosslinking reaction and performing the crosslinking at a constant volume.

The following detailed part of the description describes suitable experimental conditions to obtain the inventive hydrogels and the methods for their preparations. Also described therein are illustrative examples of the present invention, which shall not be regarded as limiting for the invention as claimed in the appended set of claims.

DETAILED DESCRIPTION OF THE DRAWINGS

Experimental

Materials and Methods

Figure 1:
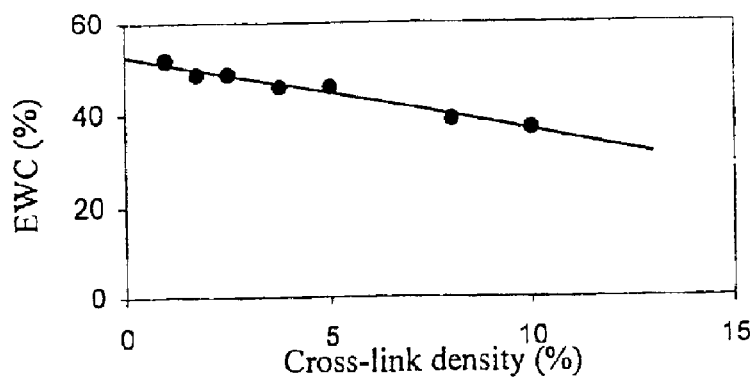
FIG. 1 shows equilibrium water content (EWC) as a function of crosslink density for a poly(1-hydroxy-1,3-propanediyl) based network (BDI.BDO.BDI crosslinker).

All reactions were performed under an inert atmosphere of nitrogen gas in flame-dried glassware.

Polyvinylalcohol (99+% hydrolyzed, Mn~130.000) was synthesized from high molecular weight polyvinylacetate (Aldrich Chemical Company Inc.) according to Sakurada, I.; Fujiwara, N. *Kobunshi Kagaku* 1945, 2, 143. Polyallylalcohol was obtained by reduction of high molecular weight polymethylacrylate with lithium aluminum hydride following Schulz, R. C.; Elzer, P. *MakromoL Chem.* 1961, 42, 205. Polyvinyl alcohol-co-ethylene (Aldrich Chemical Company Inc., ethylene content 27 mole %) and n-butylisocyanate (Aldrich Chemical Company Inc.) were used as received.

Poly(1-hydroxy-1,3-propanediyl) (PHP or "polyalcohol") was synthesized from polyketone (Carilon, LVN/[η]=6.7, Mv~450.000, Akzo-Nobel Dobbs Ferry) according to the procedure of Lommerts, B. J.; Ph.D. Thesis, University of Groningen, The Netherland, 1994. However, three additional purification steps were added. The crude PHP was dissolved in NMP (1% w/w) at 60° C. After cooling to room temperature, the solution was filtered and precipitated in diethylether. The resulting PHP was dried under reduced pressure at 50° C. This procedure was repeated three times. The purified PHP had an intrinsic viscosity of 5.5 dL/g (m-Cresol, 25 ° C). The chain extenders 1,4-butanediisocyanate (BDI) and 1,12-dodecyldiisocyanate (DDI, Aldrich Chemical Company Inc.) were distilled under reduced nitrogen pressure prior to use. The BDI.BDO.BDI chain extender was synthesized following the procedure of De Groot, et al. in *Polym. Bull.* 1998, 41, 299-306. All solvents (Acros Organics or Aldrich Chemical Company Inc.) were purified and dried according to literature procedures.

Network formation

The networks were synthesized by two different techniques using a variety of polyalcohols and solvents. Polyalcohol was dissolved in NMP, polyvinylalcohol in DMSO and polyvinyl alcohol-co-ethylene in NMP. In some cases, the polyalcohols (polyalcohol and polyvinylalcohol) were first butylated (5% or 10%) at 80° C. for 3 hours by addition of butylisocyanate in a small amount of solvent. The polymer was than precipitated in dietylether and dried under reduced pressure. Butylated polyvinylalcohol turned out to be soluble in NMP and thus crosslinking was carried out in that solvent.

Technique 1: The polyalcohol or butylated polyalcohol was dissolved in the appropriate solvent (5% w/w) and kept at 80° C. In the case of in-situ butylation, the appropriate amount of n-butylisocyanate in a small amount of solvent was added followed by 3 hours of reaction. The polyalcohol was crosslinked in solution by addition of the chain extender in a small amount of solvent. After homogeneition of the reaction mixture and 3 minutes of reaction, the reaction mixture was poured onto a petri dish and placed on a heating plate at 7° C. The solvent was allowed to evaporate at this temperature under a stream of nitrogen gas and the dry network film was post-cured at 70° C. for 20 hours. The resulting dry network was further dried under reduced nitrogen pressure at 50° C.

Technique 2: The polyalcohol was dissolved in the appropriate solvent and kept at 80° C. In some cases, the polyalcohol was butylated (5% or 10%) at 80° C. by addition of the appropriate amount of n-butylisocyanate in a small amount of solvent followed by 3 hours of reaction. Crosslinking was performed at 80° C by addition of the appropriate amount of chain extender in a small amount of solvent. After addition of the crosslinker, the reaction mixture was homogenized for 3 minutes and poured onto a glass-plate with a teflon ring. A second-glass plate was used to close the cell in such way that no gas bubbles were included. The cell with the reaction mixture was placed in an oven at 8° C. for 40 hours. Subsequently, the upper glass-plate was removed and the solvent was allowed to evaporate at 80° C. The resulting transparent networks were stored at 50° C. under reduced pressure.

Compression Molding of Polyallylalcohol

Polyallylalcohol was compression molded at 150° C. for 10 minutes. A mold with a diameter of 2 cm and a thickness of 1.5 mm was used. A force of 300 kN was applied during a Pasadena Hydrualics Inc. hydraulic press.

Network Characterization

Differential scanning calorimetry (DSC) was carried out with a Perkin-Elmer DSC-7 differential scanning calorimeter using sample weigths of 5–10 mg with a heating rate of 10° C./min. over the temperature range of –100 to 250° C.

Tensile testing was performed on rectangular-shaped specimens (40×1.0×0.35 mm), cut from thin films at room temperature using an Instron (4301) tensile tester, equipped with a 100 N load cell and an extension rate of 10 min. For determination of the permanent set, a 10 N load cell was used.

Optical transmissions were determined using a SLM Aminco 3000 Array Milton Roy spectrophotometer in the of λ=200–800 nm.

After immersing the network films in water at the appropriate temperature, equilibrium water contents (EWC) were determined using the following formula:

$$EWC(\%)=(P_{sw}-P_d)/P_{sw}$$

In which $P_{sw}$ refers to the mass of the swollen network and $P_d$ to the mass of the network in the dry state.

Polymer Syntheses

Poly(1-hydroxy-1,3-propanediyl)

Poly(1-hydroxy-1,3-propanediyl) (PHP) was synthesized from polyketone, being a stereoregular perfectly alternating copolymer of ethylene and carbon monoxide. The reduction was carried out in a 50/50 mixture of ethanol and water using sodium boron hydride as reducing agent, see Lommerts, B. J.; Ph.D. Thesis, University of Groningen, The Netherland, 1994. Although polyketone is only slightly soluble in mixtures of ethanol and water, the reduction can be carried out in this solvent system because the resulting polyalcohol is soluble. Solvation of the resulting polyalcohol is thus the driving-force for the completion of the reaction. For high molecular weight samples, long reaction times (24 h.) were needed in order to obtain complete conversion. It also turned out to be crucial to use finely powdered polyketone in order to create a large surface area. Powdering was performed at liquid nitrogen temperatures. The resulting poly(1-hydroxy-1,3-propanediyl was extensively purified by subsequent filtration and precipitation. In order to assure complete transparency of the polymer solution, this procedure was repeated three times.

Polyvinylalcohol

High molecular weight polyvinyl alcohol is not commercially available and was thus synthesized following the procedure of Sakurada et al. High molecular weight polyvinylacetate was hydrolyzed using methanol in combination with aqueous NaOH. The resulting polymer precipitated from the solution and was purified by washing with methanol. Also a commercially available EVA co-polymer (of ethylene and vinylalcohol) has been used, having 27% ethylene and 73% vinylalcohol (EVA (27/73)).

Polyallylalcohol High molecular weight polyallylalcohol was synthesized by reduction of high molecular weight polymethylacrylate with a four-fold excess of lithium aluminum hydride following the procedure of Schulz et al. The reaction was carried out in THF. The polymer, however, turned out to be insoluble in organic solvents. Only combinations of organic solvents and aqueous acid could be used, e.g. methanol1/2 M hydrochloric acid 1/1 or THF/2M hydrochloric acid 1/1. It is known that in the case of Pn<350 the polymer is also soluble in organic solvents.

Network Formation; Crosslinkers

All the described polymers, plus polyvinylalcohol-co-ethylene have been crosslinked in solution. A number of different isocyanate crosslinkers have been used. Compared with conventional acrylate crosslinkers, the main difference is that acrylates crosslinking occurs in an uncontrolled, radical reaction whereas isocyanates react in a step reaction, resulting in more homogeneous networks. As representative for a short crosslinker, 1,4-butanediisocyanate has been used. 1,12-Dodecyldiisocyanate and the BDI.BDO.BDI block have been used as longer crosslinkers. The main difference between the latter two is that 1,12-dodecyldiisocyanate is rather apolar whereas the BDI.BDO.BDI block is more polar and able to form (more) hydrogen bonds (after reaction). 1,4-Butanediisocyanate and 1,12-dodecyldiisocyanate are highly reactive whereas the BDI.BDO.BDI chain extender is far less reactive. This property is important because it allows homogeneous mixing of the reactants. The two different applied techniques will now be discussed as well as the properties of the resulting networks.

Technique 1: In this case, the polymer was dissolved at a concentration of 5% and the crosslinker was added in a small amount of solvent. After homogeneition at 80° C. the network was allowed to form at that temperature and the solvent was evaporated simultaneously. In the case of 1,4-butanediisocyanate as chain extender homogeneition was difficult due to the high reactivity of the diisocyanate. In some cases, a gel was obtained before proper mixing. After further drying of the networks under reduced pressure, the properties of the networks were determined. For each entry, a series of networks was made usually varying in crosslink percentage from 0.5 to a maximum of 20%. The different series are summarized in Table 1.

TABLE 1

Summary of polymer networks synthesized by technique 1.

| Entry | Polymer | Solvent | Crosslinker | Butylisocyanate (%) | Appearance |
|---|---|---|---|---|---|
| 1 | PHP | NMP | BDI | 0 | Opaque |
| 2 | PHP | NMP | DDI | 0 | Opaque |
| 3 | PHP | NMP | BDI.BDO.BDI | 0 | Slightly turbid |
| 4 | EVA (27/73) | NMP | BDI | 0 | Clear |
| 5 | EVA (27/73) | NMP | BDI.BDO.BDI | 0 | Clear |
| 6 | PVA | NMP | BDI.BDO.BDI | 5 | Clear |

Of the resulting polymer networks, the equilibrium water content (EWC) was determined as a function of crosslink percentage and as a function of temperature. The networks obtained by crosslinking with a short reactive isocyanate (1,4-butanediisocyanate) or a long reactive isocyanate (1,12-dodecyldiisocyanate) are opaque. This results from the high reactivity of diisocyanate, giving rise to an inhomogeneous reaction mixture. Furthermore, the apolar nature of 1,12-diisocyanate may give rise to a phase separated morphology. The BDI.BDO.BDI crosslinker has a lower reactivity than the other diisocyanates and is rather polar. The resulting networks were usually slightly turbid. At higher crosslink percentages (generally>4%), syneresis was observed for EVA and PVA based networks, indicating that in these cases elastic forces play an important role at higher crosslink percentages. The Poly(1-hydroxy-1,3-propanediyl) based networks generally did not show this effect. For the poly (alcohol) based network, the equilibrium water content as a function of crosslink percentage is shown in FIG. 1. As can be seen from FIG. 1, the equilibrium water content linearly decreases with increasing crosslink density. The decrease, however, is relatively small. The equilibrium water content is also affected by the temperature. The general trend is a decrease in EWC with increasing temperature. A representative example will be shown for Technique 2.

The copolymers of ethylene and vinylalcohol all result in transparent networks. However, the equilibrium water content is rather low in all cases although the composition in terms of hydrogen, oxygen and carbon content is comparable to poly(1-hydroxy-1,3-propanediyl) This may be caused by the blockyness of the copolymer or branching, resulting in an altered morphology. The equilibrium water content as function of crosslink density for both BDI and the BDI.BDO.BDI crosslinker in nearly constant with crosslink density and lies around 17%.

The equilibrium water content for polyvinyl alcohol is known to be rather high. However, addition of a small amount of n-butylisocyanate (5%) and crosslinking with the BDI.BDO.BDI crosslinker resulted in an equilibrium water content of 40%. So in conclusion it can be said that for a number of polymers the equilibrium water content can be influenced (tuned) by modification of the polymer with monoisocyanates or by changing the crosslink density.

Figure 2:
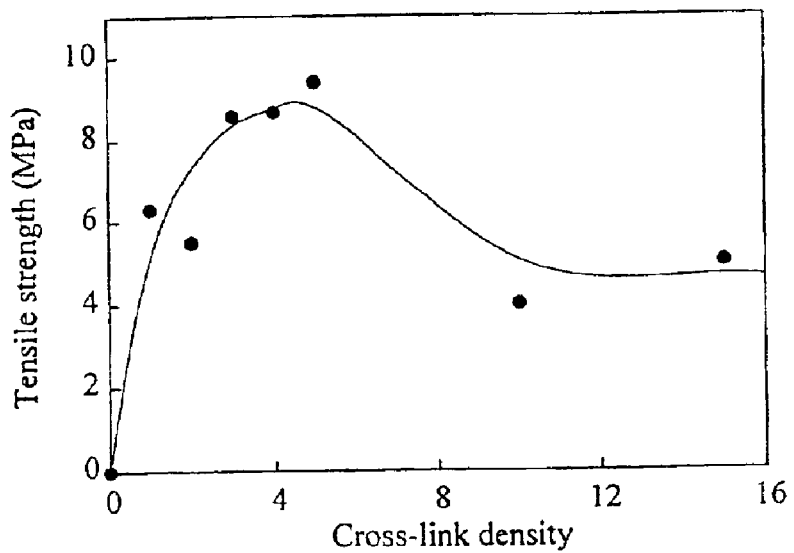
FIG. 2 shows tensile strength as a function of crosslink density for water-swollen, BDI based poly(1-hydroxy-1,3-propanediyl) network.
Figure 3:
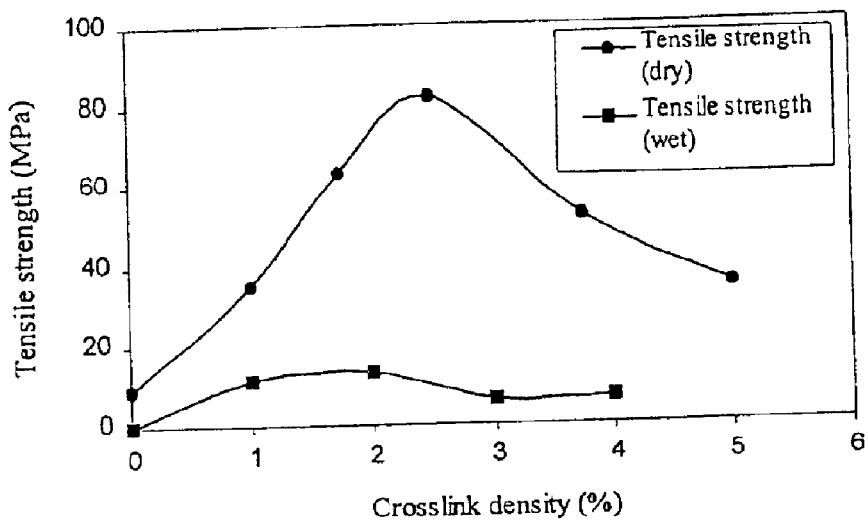
FIG. 3 shows tensile strength as a function of crosslink density for both a dry and a swollen BDI.BDO.BDI based poly(l-hydroxy-1,3-propanediyl) 1 network.

The mechanical properties of the networks were determined in dry and in swollen state, both as a function of temperature and crosslink percentage. Due to the opaque appearance of the BDI and DDI crosslinked poly(1-hydroxy-1,3-propanediyl), the main focus has been on the BDI.BDO.BDI based networks. The tensile strength as a function of crosslink density for both BDI and BDI.BDO.BDI are shown in FIGS. 2 and 3, respectively.

As can be clearly seen, both curves of the swollen networks show a maximum in the tensile strength. For the BDI.BDO.BDI crosslinker also a maximum for the dry network is visible. The first part of the curve can be explained by the decreasing amount of dangling ends with increasing crosslink density. It can also be seen that the maximum is approximately at the same position for both crosslinkers. The Young's moduli of the water-swollen networks generally vary between 1.5 and 4.0 MPa. Representative stress-strain curves will be shown for Technique 2.

For the EVA polymer networks, the same trends are observed. However, these networks show the maximum at a lower crosslinks percentage. Furthermore, they show a higher tensile strength in the swollen state. This is due to the lower equilibrium water contents of these hydrogels.

Technique 2

In technique 2, a 5% polymer solution was made and optionally n-butylisocyanate was added followed by 3 hours of reaction. Subsequently, the crosslinker was added and after homogeneition of the reaction mixture (3 minutes), it was transferred to a glass plate with a Teflon ring on it. A second glass plate and a clamp were used to close the cell and all air was excluded. After reaction, the upper glass plate was removed and the solvent was evaporated.

By using this technique, the volume during crosslinking is kept constant. This has several implications for the structure of the resulting network. In addition to the constant volume, crosslinking is performed in a good solvent (NMP) at a low concentration (4–5%). The consequences of these three factors are the following: Due to the good solvent and the low concentration, the amount of entanglements in the polymer solution has been minimized. After crosslinking, this results in networks in wherein a minimal amount of entanglements are trapped. Furthermore, it can be expected that crosslinking has occurred under homogeneous conditions.

Because the poly(1-hydroxy-1,3-propanediyl) networks (synthesized by method 1) showed the most promising behavior, Technique 2 was also applied to this polymer. Furthermore, in order to keep the equilibrium water content high and the modulus low, a small amount of crosslinker was used. The networks that have been synthesized by this method are summarized in Table 2.

TABLE 2

Networks synthesized by Technique 2.

| Entry | Polymer | Solvent | Crosslinker and amount (%) | Butylisocyanate (%) | Appearance |
|---|---|---|---|---|---|
| 1 | PA | NMP | 0.5% BDI.BDO.BDI | 0 | Clear |
| 2 | PA | NMP | 0.5% BDI.BDO.BDI | 5 | Clear |
| 3 | PA | NMP | 0.5% BDI.BDO.BDI | 10 | Clear |

These networks were all clear. This probably results from the more homogeneous reaction conditions. The equilibrium water content as a function of crosslink generally shows the same behavior as in the case of technique 1. Also the equilibrium water content as a function of temperature was determined. A representative example (poly(1 -hydroxy-1, 3-propanediyl) system 1) is shown in FIG. 4.

Figure 4:
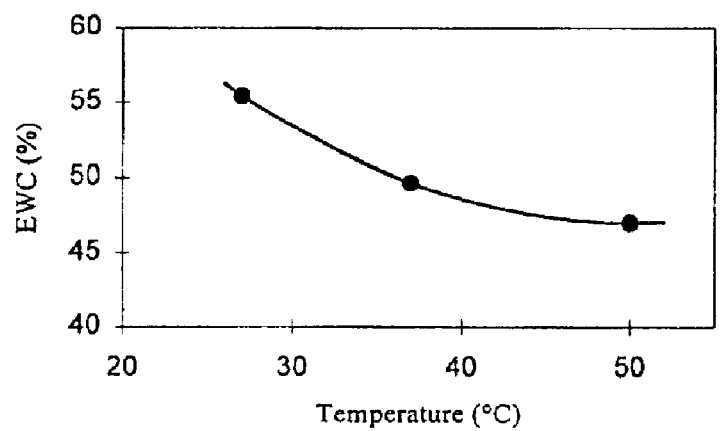
FIG. 4 shows the equilibrium water content as a function of temperature for poly(1-hydroxy-1,3-propanediyl) network 1.

As can be seen from FIG. 4, higher temperatures result in more polymer-polymer interactions and thus a decreased solubility (LCST). However, in this case of a low crosslink density and in the absence of n-butylisocyanate the system turned out to be rather unstable. A sudden increase or decrease in the temperature often resulted in opaqueness or even a complete loss of transparency. Sudden change in environment (e.g. removal of the water surrounding the gel) had the same result.

Figure 5:
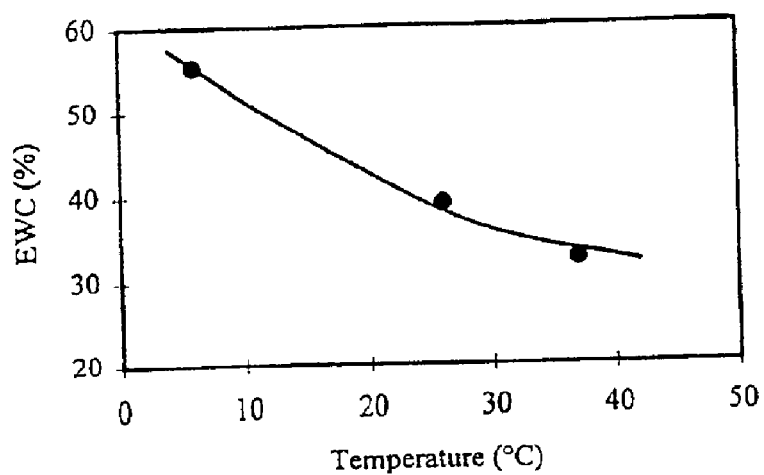
FIG. 5 shows equilibrium water content as a function of temperature for polyalcohol network 2.

The most likely explanation for this effect is that the homogeneity of the system is disturbed resulting in a phase-separated morphology in which concentrated polymer phases are present as well as dilute polymer phase. In order to test this hypothesis, small amounts of n-butylisocyanate were added before crosslinking in order to avoid phase-separation and eventually crystallization. The resulting network (5% n-butylisocyanate, 0.5% BDI.BDO.BDI crosslinker) was transparent and, as expected, far more stable to changes in temperature and environment. Also in this case, the equilibrium water content has been determined as a function of temperature (FIG. 5).

Figure 6:
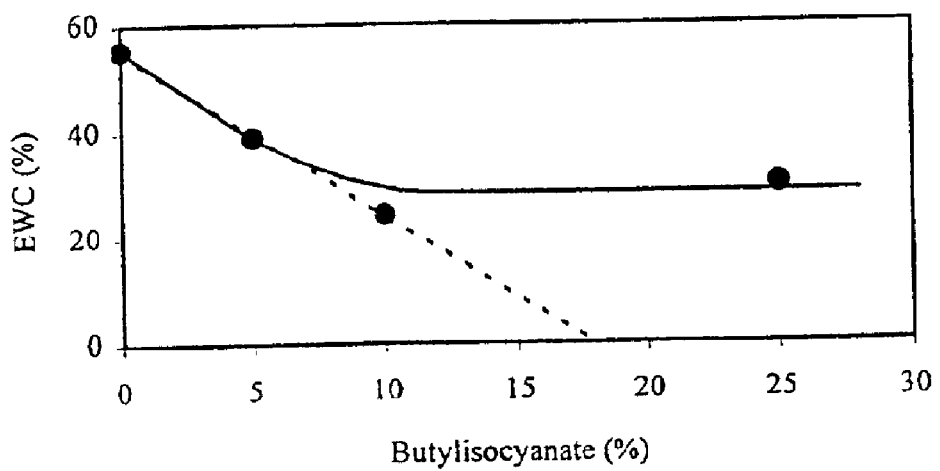
FIG. 6 shows equilibrium water content as a function of n-butylisocyanate percentage.

As can be seen, the general trend is comparable to network 2. However, due to the less hydrophilic nature of the n-butylurethane moiety compared to the hydroxyl group, the equilibrium water content has decreased over the whole temperature range. When more n-butylisocyanate is added, the equilibrium water content becomes relatively stable again. The equilibrium water content as a function of n-butylisocyanate groups is shown in FIG. 6.

From this, it can be concluded that the equilibrium water content of the gels can be influenced both by the addition of side group and the crosslink percentage. When higher equilibrium water contents are desired, n-butylisocyanate can be replaced by a less hydrophobic isocyanate like ethylisocyanate. Phenylisocyanate may be an interesting alternative in order to enhance the refractive index of the system. This may, however, lead to yellowing of the gel on exposure to light.

Because the equilibrium water content is rather strongly influenced by the amount of side groups and less by the percentage of crosslinker (vide infra) it is in principle possible to vary the crosslinking percentage without affecting the equilibrium water content (within certain limits). A further experiment that has been performed is determination of the equilibrium water content in buffered phosphate solution (saline). At 37° C., in case of polyalcohol system 2, a small increase from 32% to 36% equilibrium water content was observed which is satisfactory for the application.

Functionalization with n-butylisocyanate can furthermore be applied to polymers that show too high equilibrium water contents for the application. When e.g. polyvinylalcohol is functionalized with n-butylisocyanate, the equilibrium water content can be adjusted to approximately 40%. This 40% was found in the case where the amount of hydroxyl functionalities in PVA was reduced to level in which they are present for polyalcohol. The water-swollen network showed a tensile strength of 5.0 MPa.

Figure 7:
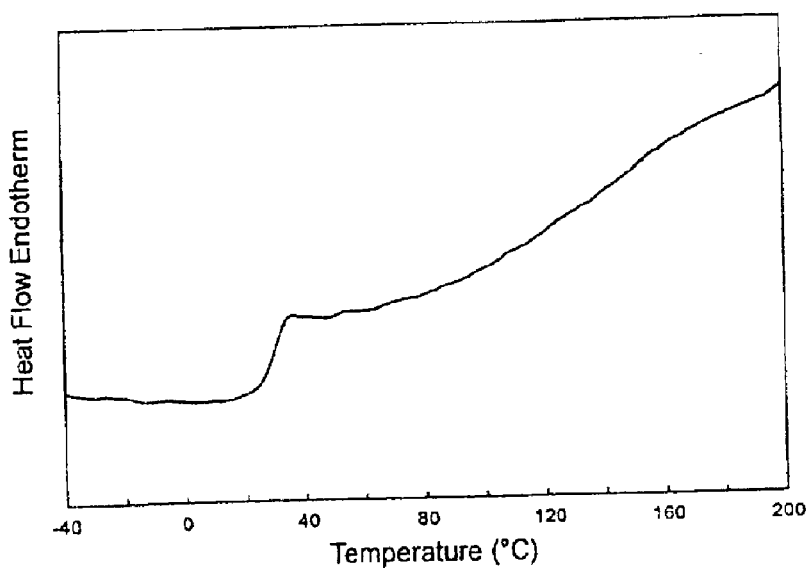
FIG. 7 shows DSC traces of polyalcohol system 2:0.5% crosslinker and 5% n-butylisocyanate.
Figure 8:
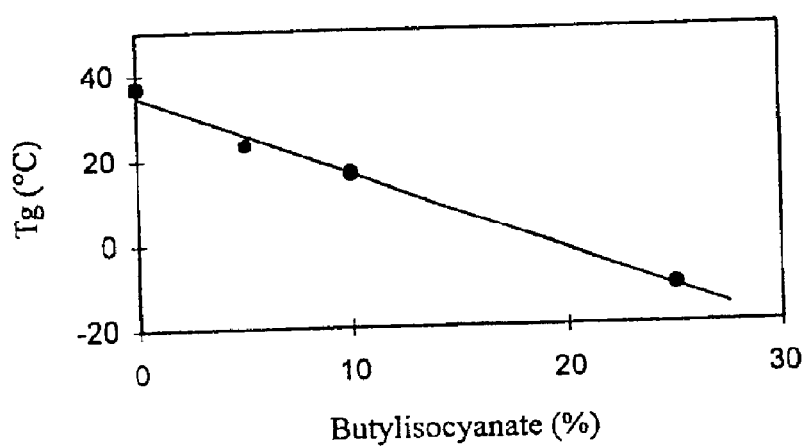
FIG. 8 shows the dependence of the Tg on the percentage of side groups.

In view of transparency and mechanical properties, the thermal behavior of the network is of great importance. For polyalcohol system 2, DSC traces are shown in FIG. 7. Apparently, only small amounts of crosslinker and side groups are required to eliminate the crystallinity. The melting point of pure polyalcohol is usually found at approximately 120° C. The Tg is found at 25° C. allowing folding of the material at room temperature. Compared to uncrosslinked polyalcohol, the Tg has been lowered by 15–20° C. The dependence of the Tg on the percentage of n-butyl functionalization is shown in FIG. 8.

The poly(1-hydroxy-1,3-propanediyl) networks with 0–5% of side groups look most promising for the application since their equilibrium water content is still high enough.

Approximately 5% of side chains are preferred since this prevents phase separation in the swollen gel. The optical transmission of the hydrogel with 5% n-butylisocyanate at λ=480 nm was found to be>90%.

Figure 9:
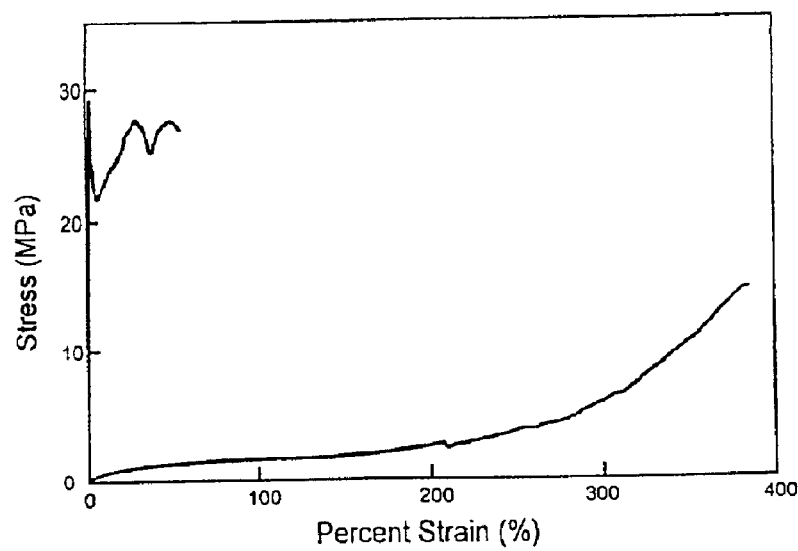
FIG. 9 shows a stress-strain curve of poly(l-hydroxy-1,3-propanediyl network with 5% n-butylisocyanate and 0.5% BDI.BDO.BDI crosslinker; dry and water-swollen.

The low crosslinking percentage has consequences for the mechanical properties of both the dry and the swollen networks. A representative stress-strain curve the 5% butylated and 0.5% crosslinked network in both dry and swollen state is shown in FIG. 9.

In the dry state, the network has a tensile strength of ~30 MPa. For this specific crosslink density, this is in the same order as comparable networks synthesized by technique 1 (FIG. 3). After swelling in water, the (uncorrected) tensile strength has decreased by a factor 2 (15 MPa). The water-swollen network still has a considerable Young's modulus but at strains greater than 50%, the modulus approaches 0. The somewhat higher modulus at the beginning of the curve may be caused by the disruption of small crystallites. However, DSC measurements did not reveal any crystallinity. The low modulus after 50% strain is caused by the absence of entanglements, allowing the polymer chains to rearrange freely on increasing strain. This feature is important in order to apply these types of networks for accommodating lens systems. At the end of the curve, an upturn effect is observed, indicating oriented crystallization. The stress-strain curves of dry poly(1-hydroxy-1,3-propanediyl) networks with different amounts of n-butylisocyanate groups are shown in FIG. 10.

Figure 10:
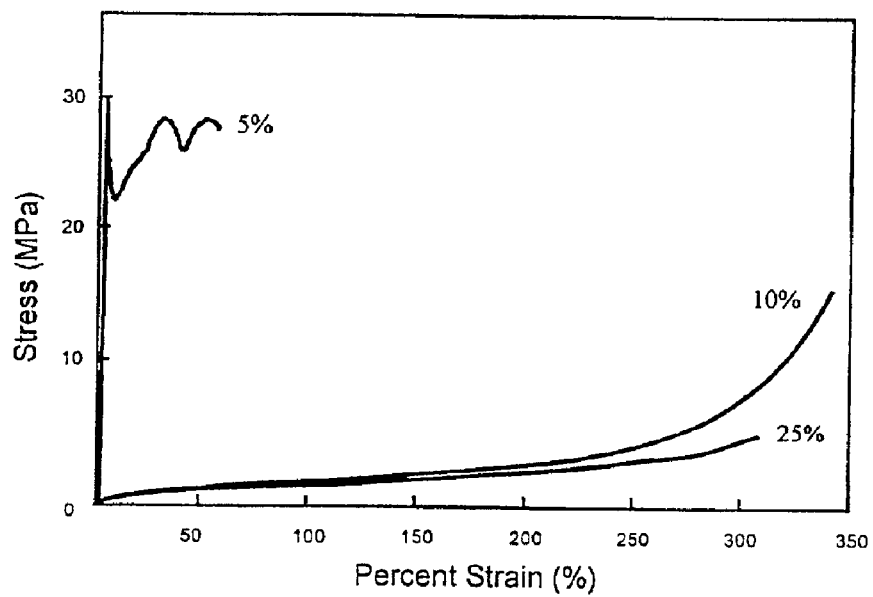
FIG. 10 shows stress-strain curves of dry poly(1-hydroxy-1,3-propanediyl) networks with 5, 10 and 25% of n-butylisocyanate groups.
Figure 11:
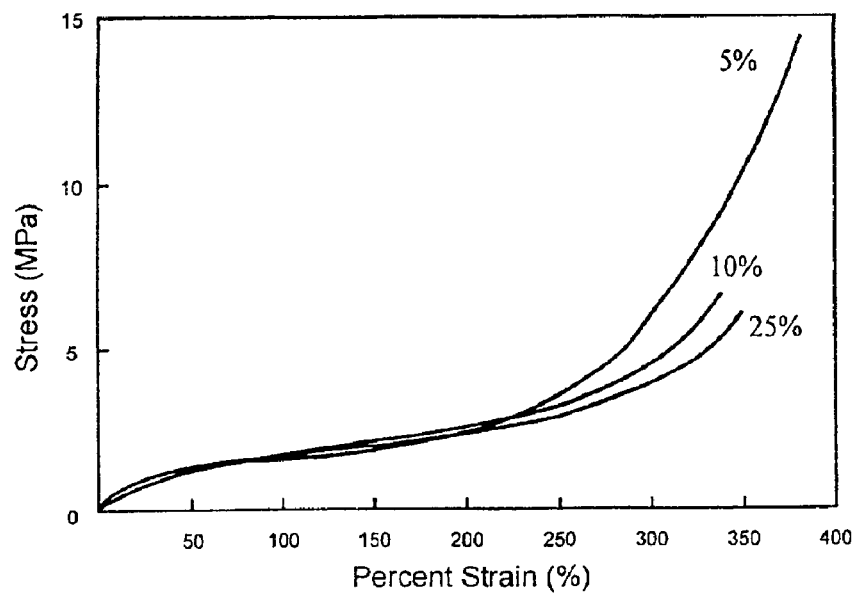
FIG. 11 shows stress-strain curves of water swollen poly(1-hydroxy-1,3-propanediyl) networks with 5, 10 and 25% of n-butylisocyanate groups.

In FIG. 10, two effects can be observed. In case of 5% side groups, the Tg was observed approximately at room temperature and the material has a rather high modulus. When 10% of n-butylisocyanate was added, the Tg decreases to 18° C. (FIG. 8) and the modulus decrease dramatically. At the end of the curve, an upturn effect is observed 40 indicating oriented crystallization. When the amount of side groups is increased to 25% oriented crystallization is prevented and the upturn effect vanishes. The stress-strain curve of the corresponding hydrogels is shown in FIG. 11.

In the case of water-swollen networks, the Tg's have decreased to values below room temperature and all hydrogels exhibit identical stress-strain behaviors up to 250% strain. However at higher strains the network with 5% side groups shows a considerable up-turn effect indicating oriented crystallization. Also viscoelastic contributions may play an important role, since the Tg was found near room temperature. In the case of more side groups these effects decrease.

Figure 12:
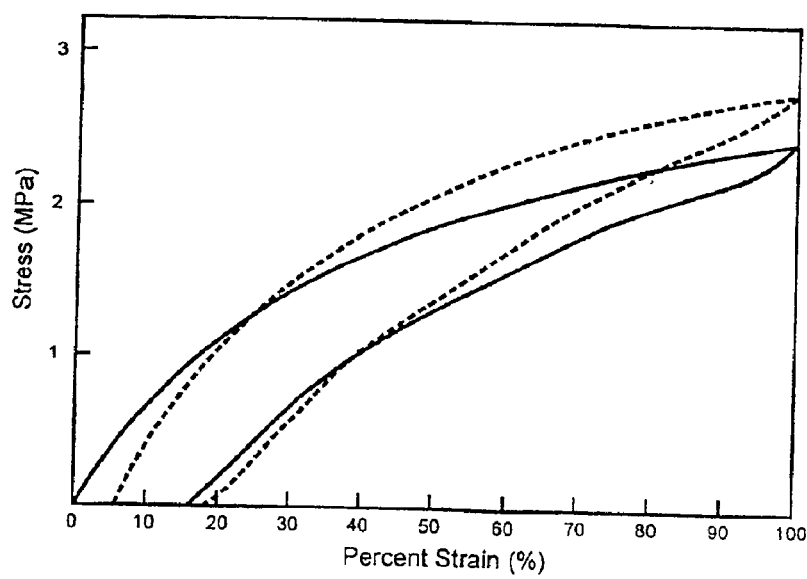
FIG. 12 shows the determination of the permanent deformation of polyalcohol network 2;-first cycle; . . . third cycle.

Considering accommodating lens system it is important to study the permanent deformation of the water-swollen networks. The gel was cyclically deformed two times to 100% strain. After three minutes, a third cycle was recorded. The first and the third cycle are shown in FIG. 12. As can be seen from FIG. 12, the permanent deformation lies around 5%, which is rather low. A hysteresis loop is observed indicating non-ideal rubber behavior. In the third cycle, an increase in modulus is observed. This results from the slow evaporation of water out of the gel. The permanent deformation and the hysteresis loop are indications that small crystallites are present. The networks, however, are clear indicating that the crystallites are smaller than the wavelength of light.

Compression molding

Figure 13:
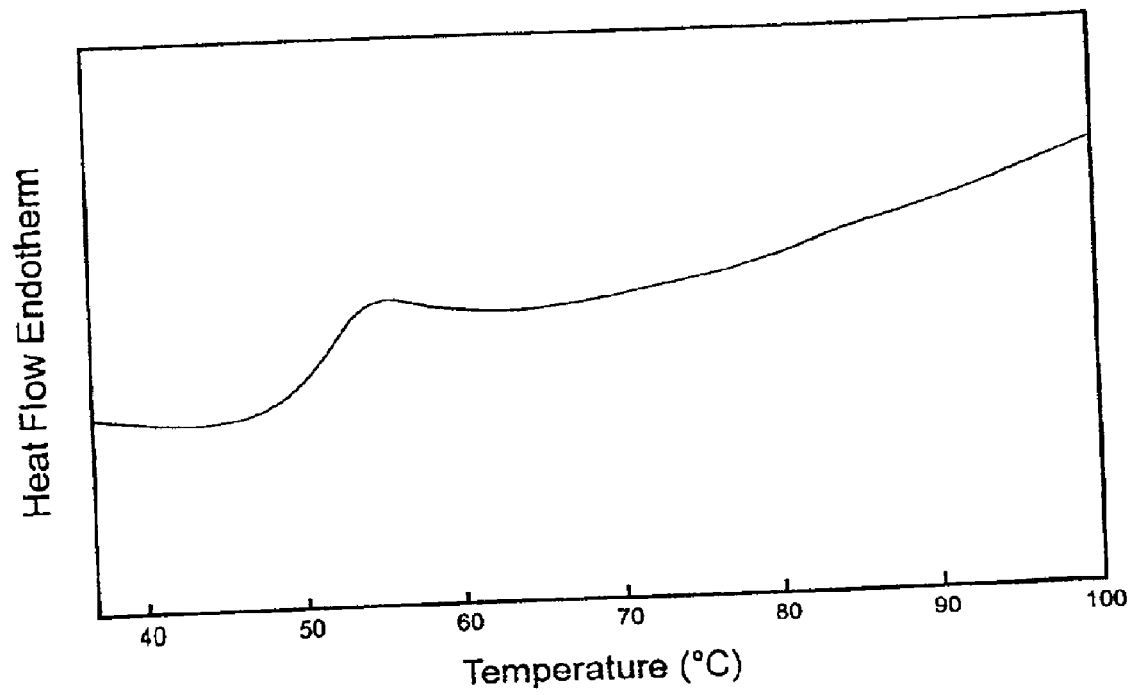
FIG. 13 shows a DSC thermogram of dry polyallylalcohol.

Since high molecular weight polyallylalcohol is insoluble in organic solvents, the polymer was processed by compression molding at 150° C. The DSC thermogram showed a Tg at 52° C. and no indication of crystallinity, see FIG. 13. The brittle and dry polymer was swollen in water at 25° C. and the equilibrium water content of the corresponding transparent soft polymer gel was determined to be 45%. This value is in the same order as the poly(1-hydroxy-1,3-propanediyl) networks and makes the material suitable for the application. Although the polymer is insoluble in water and reptation of polymer chains is expected to be slow crosslinked systems are preferred in view of permanent set on deformation. An interesting possibility is to swell small polyallylalcohol particles in crosslinker solution followed by removal of the solvent and compression molding. Bu such a method a homogenous polymer/crosslinker mixture can be obtained resulting in homogenous polymer networks after crosslinking.

What is claimed is:

1. A hydrogel comprising a network of hydrophilic polymer having hydroxyl group-carrying carbon to carbon backbones and having a tensile strength of at least 1 MPa, wherein the network is formed by crosslinks in the hydrophilic polymer.

2. A hydrogel comprising a network of hydrophilic polymer having hydroxyl group-carrying carbon to carbon backbones and having a tensile stretch of at least 1 MPa and an elasticity modulus less than about 10 kPa.

3. A hydrogel according to claim 1 having a tensile strength of at least about 5 MPa.

4. A hydrogel according to claim 1 having an elongation of at least 50% at equilibrium water content.

5. A hydrogel comprising a network of hydrophilic polymer having hydroxyl group-carrying carbon to carbon backbones and having a tensile strength of at least 1 MPa and sufficient optical clarity so as to obtain an optical transmission of at least about 40%.

6. A hydrogel comprising a network of hydrophilic polymer having hydroxyl group-carrying carbon to carbon backbones and having a tensile strength of at least 1 MPa and a refractive index of at least about 1.40.

7. A hydrogel comprising a network of hydrophilic polymer having hydroxyl group-carrying carbon to carbon backbones and having a tensile strength of at least 1 MPa, wherein the hydrophilic polymer has a molecular weight of at least 200,000.

8. A hydrogel according to claim 1 having a polymer content of about 30 to 80% (wt).

9. A hydrogel comprising a network of hydrophilic polymer having hydroxyl group-carrying carbon to carbon backbones and having a tensile strength of at least 1 MPa, wherein the hydrophilic polymer is chemically modified with agent capable of reducing its equilibrium water content.

10. A hydrogel according to claim 9, wherein said agent is a monoisocyanate.

11. A hydrogel according to claim 10, wherein said monoisocyanate is a lower alkyl, aryl or arylalkyl isocyanate.

12. A hydrogel according to claim 1 wherein the hydrophilic polymer is at least one selected from the group consisting of —($CH_2$—CHOH)$_n$—(polyvinyl alcohol); —($CH_2$—$CH_2$)$_n$($CH_2$—CHOH)$_m$—(copolymer of ethylene and vinyl alcohol); —($CH_2$—$CH_2$—CHOH)$_n$—(poly(1-hydroxy-1,3-propanediyl)); and —($CH_2$—CH($CH_2$OH))$_n$—(polyallyl alcohol).

13. A hydrogel comprising a network of hydrophilic polymer having hydroxyl group-carrying carbon to carbon backbones and having a tensile strength of at least 1 MPa, wherein the hydrophilic polymer is polyallyl alcohol.

14. A hydrogel comprising a network of hydrophilic polymer having hydroxyl group-carrying carbon to carbon backbones and having a tensile strength of at least 1 MPa, wherein the network is formed by crosslinks in the hydrophilic polymer and wherein the crosslinking density is less than about 10%.

15. A hydrogel according to claim 14 crosslinked by a diisocyanate.

16. A hydrogel according to claim 15, wherein said diisocyanate has a formula OCN—($CH_2$)$_4$—NH—C(O)O—($CH_2$)$_4$—O(O)C—NH—($CH_2$)$_4$—NCO.

17. A hydrogel according to claim 15 having crosslinks of the formula —O—C(O)—NH—R—NH—C—(O)—O—, wherein R is a spacing group.

18. A hydrogel according to claim 17, wherein R is an optionally substituted lower alkyl group having one to ten carbon atoms.

19. A hydro gel according to claim 18, wherein R is —($CU_2$)$_4$—.

20. A hydrogel comprising a network of hydrophilic polymer having hydroxyl group-carrying carbon to carbon backbones and having a tensile strength of at least 1 MPa, wherein the hydrophilic polymer is crosslinked by an epoxy compound.

21. A hydrogel comprising a network of hydrophilic polymer having hydroxyl group-carrying carbon to carbon backbones and having a tensile strength of at least 1 MPa, wherein the hydrophilic polymer is poly(1-hydroxy-1,3-propanediyl).

22. A hydrogel according to claim 21 crosslinked with diisocyanate.

23. A hydrogel comprising poly(1-hydroxy-1,3-propanediyl) crosslinked with a lower alkyl diisocyanate.

24. A hydrogel according to claim 23, wherein said lower alkyl diisocyanate is 1,4-butanediisocyanate.

25. A hydrogel according to claim 23, wherein the hydroxyl groups of poly(1-hydroxy-1,3-propanediyl) are modified with a monoisocyanate before being crosslinked with a lower alkyl diisocyanate.

26. An implant made of a hydrogel according to claim 1.

27. An ophthalmic lens made of a hydrogel according to claim 1.

28. An ophthalmic lens made of a hydrogel comprising a network of hydrophilic volumes having hydroxyl group-carrying carbon to carbon backbones and having a tensile strength of at least 1 MPa and having (a) an elasticity modulus less than about 10 kPa;

(b) a tensile strength of at least about 1 MPa;

(c) an elongation of at least 50% at equilibrium water content;

(d) sufficient optical clarity so as to obtain an optical transmission of at least about 40%; and (e) a refractive index of at least about 1.40.

29. A hydrogel according to claim 2, wherein the elasticity modulus is less than about 5 kPa.

30. A hydrogel according to claim 7, wherein the hydrophilic polymer has a molecular weight of at least 300,000.

31. A hydrogel according to claim 8, having a polymer content of about 40 to 70% (wt).

32. A hydrogel according to claim 14, wherein the crosslinking density is less than about 5%.

33. An ophthalmic lens according to claim 28, wherein the elasticity modulus is less than about 5 kPa.

* * * * *

UNITED STATES PATENT AND TRADEMARK OFFICE
CERTIFICATE OF CORRECTION

PATENT NO. : 6,846,875 B2
DATED : January 25, 2005
INVENTOR(S) : Albert J. Pennings et al.

It is certified that error appears in the above-identified patent and that said Letters Patent is hereby corrected as shown below:

Column 13,
Line 35, change "—$(CU_2)_4$—" to -- —$(CH_2)_4$— --

Signed and Sealed this

Fifth Day of July, 2005

JON W. DUDAS
*Director of the United States Patent and Trademark Office*